United States Patent
Purtschert et al.

[11] Patent Number: 5,168,323
[45] Date of Patent: Dec. 1, 1992

[54] DEVICE AND METHOD FOR DETERMINING IMPURITIES IN A GAS

[75] Inventors: Werner Purtschert; Joerg Broder, both of Winterthur, Switzerland

[73] Assignee: Sulzer Brothers Limited, Winterthur, Switzerland

[21] Appl. No.: 319,617

[22] Filed: Mar. 6, 1989

[30] Foreign Application Priority Data

Mar. 31, 1988 [CH] Switzerland .................... 1234/88

[51] Int. Cl.$^5$ .................... G01J 3/443; G01N 21/67
[52] U.S. Cl. .................... 356/313
[58] Field of Search .................... 356/311, 313, 314

[56] References Cited

U.S. PATENT DOCUMENTS

| | | | |
|---|---|---|---|
| 2,509,649 | 5/1950 | Norman | 356/311 |
| 2,855,820 | 10/1958 | Robinson | |
| 3,951,607 | 4/1976 | Fraser | 250/226 |
| 4,801,209 | 1/1989 | Wadlow | 356/311 X |

FOREIGN PATENT DOCUMENTS

| | | | |
|---|---|---|---|
| 655858 | 1/1963 | Canada | 356/313 |
| 0192919 | 9/1986 | European Pat. Off. | |
| 1087832 | 8/1960 | Fed. Rep. of Germany | |
| 0188591 | 11/1966 | U.S.S.R. | |

OTHER PUBLICATIONS

R. Ikan, et al., Organic Chemistry: Compound Detection, Encyclopedia of Physical Science and Technology, vol. 10, pp. 43 and 54–56.
R. J. Walker, Detector for Trace Amounts of Nitrogen in Helium, Cryogenics, vol. 26, May 1986, pp. 297–299.

Primary Examiner—Vincent P. McGraw
Attorney, Agent, or Firm—Kenyon & Kenyon

[57] ABSTRACT

A device for determining small amounts of impurities in gases comprises a measuring cell in which an arc is generated with a low frequency alternating voltage source between two electrodes. The emission spectrum of the arc is observed by means of interference filters and photosensors and the concentrations of the impurities are determined in the electronic evaluation unit for the spectral intensities typical of the impurity traces. The device is suitable for the continuous measurement of small quantities of gaseous impurities for example traces of nitrogen, argon, neon, water vapor, gaseous hydrocarbon, in helium.

6 Claims, 4 Drawing Sheets

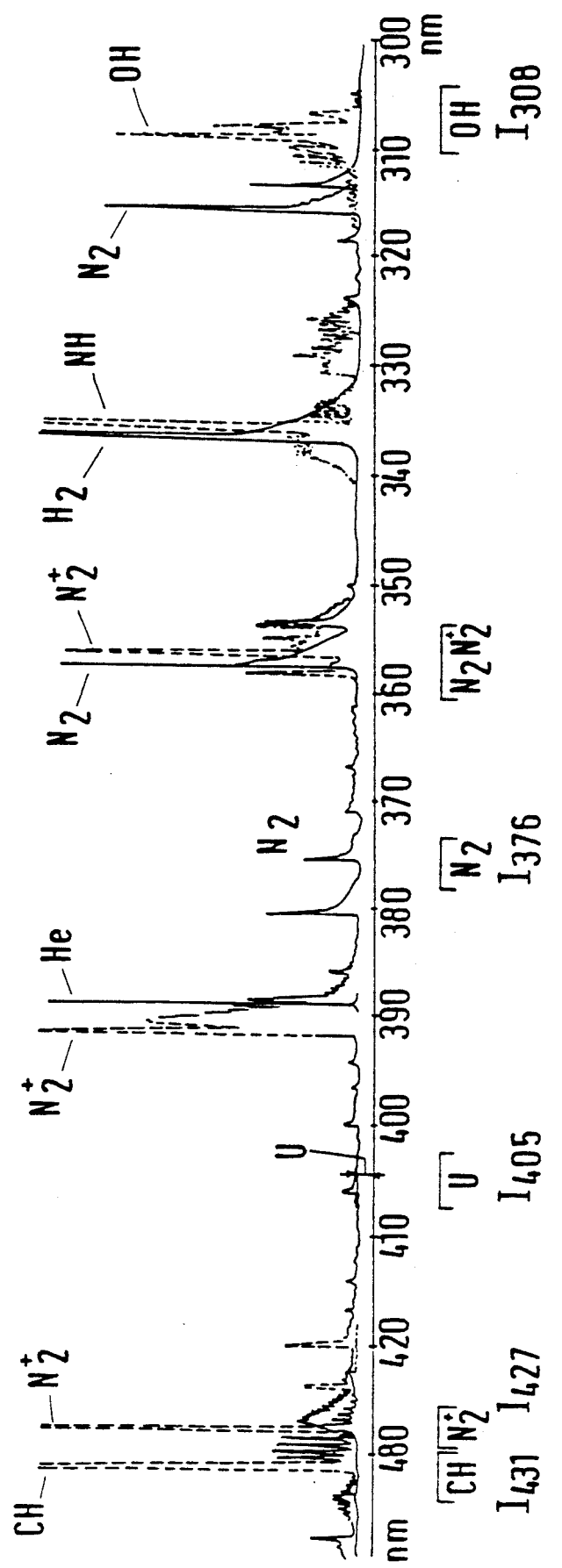

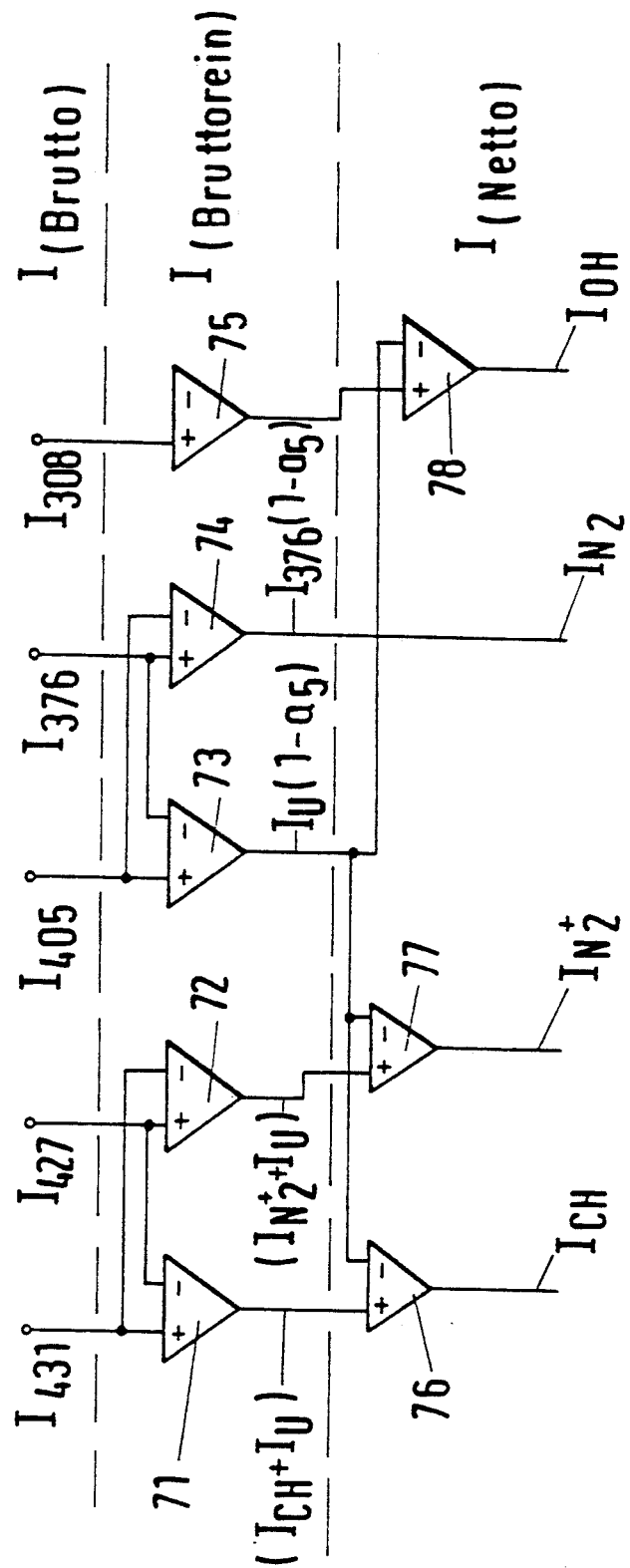

DEVICE AND METHOD FOR DETERMINING IMPURITIES IN A GAS

This invention relates to a device and method for determining impurities in a gas. More particularly, this invention relates to a device and method for determining trace amounts of impurities in a noble gas.

Heretofore, various techniques have been employed for the determination of small amounts of impurities in gases, such as noble gases, on the basis of an emission spectrum of the contaminated gas. Generally, these techniques have been employed to determine very small residual gas amounts or residual gas contaminations in concentrations of about 1 to 50 ppm (volume) or less in noble gases such as, helium, Neon or Argon. However, these techniques have only been reliable under laboratory conditions or conditions similar thereto. Such a laboratory device for the measurement of nitrogen traces in helium has been described, for example, in the journal "Cryogenics", Vol. 26, May, 1986, pages 297-299 in the article "Detector For Trace Amounts of Nitrogen in Helium" R. J. Walker. As described, the detector employs a pair of electrodes to define an arc cell in order to establish a low current electrical discharge in the gas and both electrodes are connected to a regulated DC power supply of 0 to 3 kV. However, such devices do not permit a continuous monitoring of gas impurities since the using up and/or the changing of the electrodes does not permit a reliable continuous measurement operation over long time periods.

U.S Pat. Nos. 2,855,820 and 3,951,607 also describe various techniques for the spectroscopic analysis of gases and vapors. In the first case, a D. C. or low frequency discharge can be used to permit spectroscopic analysis of helium. In the latter case, the constituents of a patient's breath is determined in an analyzing chamber to which a voltage difference can be applied.

Analytical pyrolysis has also been used in gas chromatography to determine the constituents of a gas. Such a technique has been described in Encyclopedia of Physical Science and Technology, Vol. 10, Academic Press, Inc., 1987 (London, GB), R. Ikan, et al "Organic Chemistry: Compound Detection", pages 54 to 56.

It is an object of this invention to provide a reliable device for the measurement of impurities in a gas over a long period of time.

It is another object of the invention to provide a method of determining impurities in a gas over time periods of weeks or months.

It is another object of the invention to increase the useful life of a device for determining impurities in a gas delivered to an arc for an emission spectrum.

Briefly, the invention provides a device for determining impurities in a gas which comprises a measuring chamber having means for generating an electrical discharge in a gas to be measured, a low frequency alternating voltage source connected to the means and means for measuring and evaluating an emission spectrum of the gas.

The means for generating the electrical discharge is in the form of a pair of electrodes which define a gap therebetween for the generation of an arc into which the gas may pass for generation of an emission spectrum. Each electrode is constructed with a conically shaped end with a cylindrical tip having an area approximately equal to the base of the generated arc.

The invention also provides a method of determining impurities in a noble gas. In accordance with the method, an electrical discharge is generated within a chamber under a low frequency alternating voltage, a gas is passed through the electrical discharge to obtain an emission spectrum of the gas and the emission spectrum is measured and evaluated in order to determine the impurities therein. For example, the gas may be helium while the impurities to be detected are in the group consisting of nitrogen, oxygen, argon, neon, gaseous hydrocarbons ($C_xH_y$), water vapor and hydrogen. Also, other noble gas amounts may be sensed within the main gas flow.

By using a low frequency alternating voltage source in a frequency region of, for example, less than 1 kHz for the electrodes, the wearing away of the electrode tips can be practically eliminated. This also permits a higher continuous working period to be achieved with a life time of a few hundred to a few thousand hours for the electrodes.

Although other shapes for the construction of the electrode tip are suitable, the embodiment in which the surface of the tip at least approximates the area of the base of the arc in operation has been found to be particularly favorable for spectrometric observation. With the cylindrical tip mounted on a truncated conical end, the glow discharge remains particularly well concentrated in the desired position.

The frequency of the low frequency alternating current source may be selected to be in the frequency region of less than 1 kHz for example a frequency reaching of about 50 Hz. The voltage may be selected in the order of magnitude of about 1500 V, but may alternatively lie in the region of several kV. The strength of the arc current lies for example in the order of magnitude of several mA. The electrode spacing lies, for example, in the region of a few millimeters. The pressure in the measuring cell of the arrangement may lie in the order magnitude of about one to two Bar.

The device can be used for the simultaneous determination of a plurality of different very small amounts of impurities in the range of a fraction of one ppmv (ppm in volume unit) to several hundred ppmv. Such a device comprises, for each impurity component to be determined, a filter which is characteristic for the spectral lines of this component, for example an interference filter and a photosensor sensitive for this light, for measuring the intensity of the relevant spectral lines. Simply said, the intensity of the various spectral lines which are characteristic for the particular impurities, is a measure for the concentration of an impurity. In any event, it has to be taken into account that the intensity—observed at a given wavelength—is superimposed on a background. The effective intensity orginating from the impurity, is computationally determined from linear combinations of the various measured intensities. The computational evaluation, i.e. the forming of the linear combinations and further magnitudes can be done With an analog or a digital computer, to which the amplified signals of the intensities measured with the photosensors are fed.

The device is also suitable for determining the oil-aerosol content in a gas, and in this case the device uses a pyrolyzer and the measurement is effected intermittently.

These and other objects and advantages of the invention will become more apparent from the following detailed description taken alone or in combination with the following:

FIG. 1 illustrates a simplified block diagram of a device according to the invention for determining residual gas amounts;

FIG. 2 diagrammatically illustrates a device according to the invention with a pyrolyzer with which contamination with aerosols can be determined;

FIG. 3 illustrates an example of intensity variations of an emission spectrum of an arc in helium with various residual gas contaminates in dependence on the wave length as measured with a device according to the invention;

FIG. 4 illustrates a basic diagram of an analog electric circuit for forming the linear combinations of the measured intensities and for calculating the effective intensities (net intensities) produced by the contaminants in the spectral region typical of the contaminant.

Figure 1:
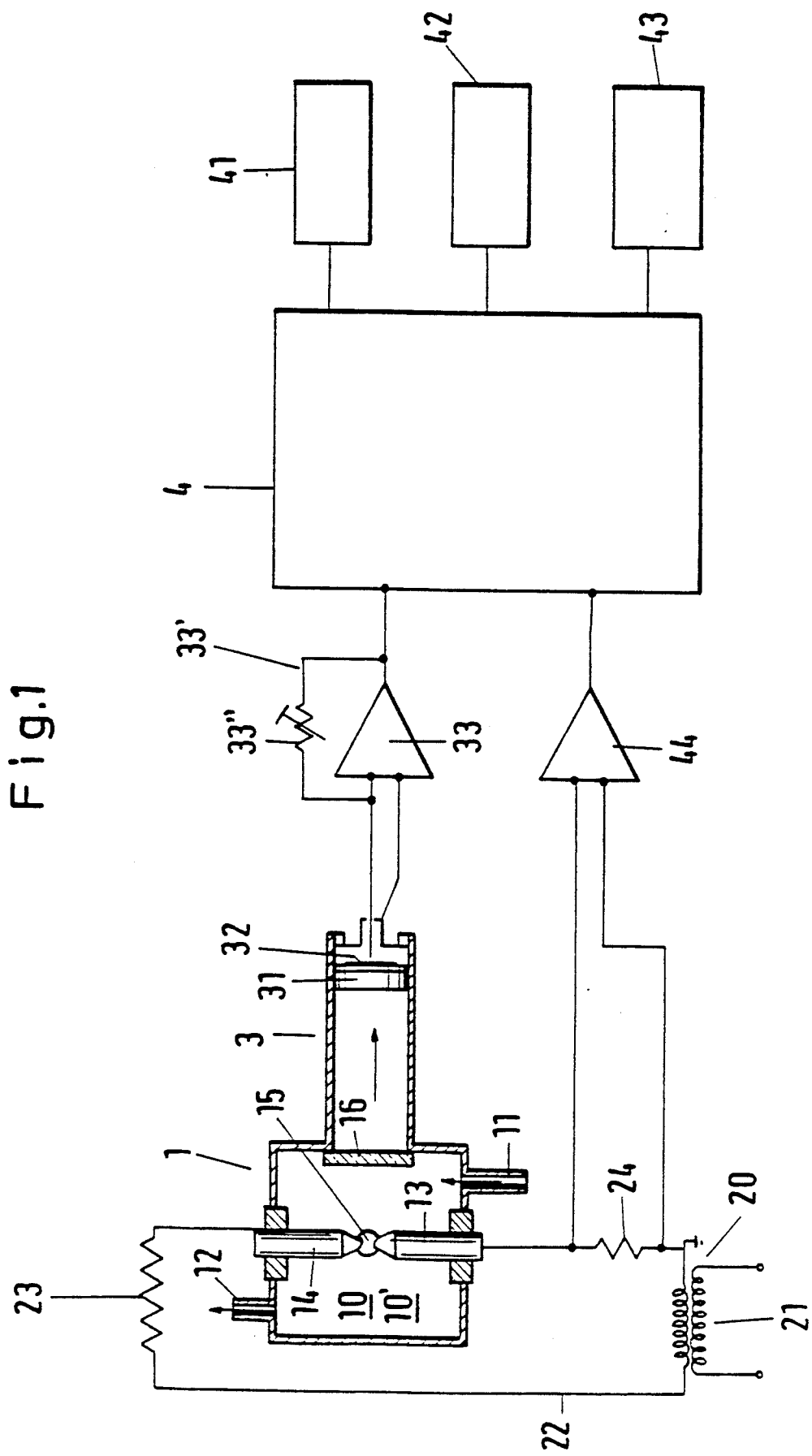

Referring to FIG. 1, the device for determining impurities in a gas, such as a noble gas, includes a gas-tight measuring chamber or measuring cell 1 which is filled with the gas 10 to be measured. The gas may be a cryogas from a cryogenic gas liquefier, e.g. helium from a helium liquefying plant having traces of gaseous impurities 10', such as, one or more of nitrogen, neon, argon, water vapor, and gaseous hydrocarbon. As indicated, the measuring chamber 1 has an inlet 11 for supplying gas into the chamber 1 and an outlet 12 for an outflow of gas from the chamber 1. In addition, the measuring chamber 1 has means, such as a pair of electrodes 13, 14, for generating an electrical discharge in the gas to be measured. As indicated, the electrodes 13, 14 are spaced apart within the measuring chamber 1.

A low frequency alternating voltage source/alternating current source, in the form of a transformer 20, is connected to the electrodes 13, 14. As indicated, the transformer 20 has a primary circuit 21 as well as a secondary circuit 22 which is connected to the electrodes 12, 13 for generating an arc 15 between the electrodes 13, 14 in order to effect an emission spectrum of the gas. The secondary circuit 22 also has two resistances 23, 24 disposed to opposite sides of the measuring chamber 1. The arc current lies, for example, between 10 and 20 mA.

The device also includes an electronic means 4 for measuring and evaluating the emission spectrum of the gas in the electrical discharge in order to determine the concentration of impurities therein. In addition, a sensing chamber 3 is disposed between the measuring chamber 1 and the measuring means 4.

The sensing chamber 3 is disposed in line with a gas-tight window 16 of the measuring chamber 1. This window 16 is transmissive for light in the frequency range important for the measurement, for example, a window of quartz glass. The sensing chamber 3 includes a spectral selective filter, for example, an interference filter 31 for filtering the emission spectrum in order to selectively transmit spectral lines of a selected trace gas. In addition, a photosensor such as a photodiode 32 is disposed downstream of the filter 31 in order to generate an electrical signal in response to the transmitted spectral lines from the filter 31 for transmission to the measuring means 4.

The electric signals generated in the photosensor 32 are amplified in an amplifier 33 and linearized and processed in the electronic evaluation means 4. The output signal from the amplifier 33 can be standardized by means of a circuit 33' having a variable resistance 33''.

During operation, an electrical discharge (arc 15) is generated within the measuring chamber 1 under a low frequency the electrical discharge to obtain an emission spectrum of the gas. This spectrum is then transmitted through the window 16 into the measuring chamber 3 wherein the spectrum is filtered and a respective electrical signal generated by the respective filter 31 and photosensor 32. The resulting signal is then transmitted via the amplifier 33 to the electronic evaluation means 4. The spectral composition (emission spectrum) is then investigated and from that the concentration of the contaminant(s) determined.

The above described device is suitable for measuring and determining concentrations of a single residual gaseous contaminate 10', for example, nitrogen in a gas 10 such as helium.

In order to determine the concentrations of a plurality of trace gases, a filter for each trace gas is arranged in the sensing chamber 3 along with a photosensor so that suitable signals can be supplied via the amplifier 33 to the electronic evaluation means 4. In this case, the interference filter 31 is selectively transmissive for spectral lines of a respective particular trace gas. In addition, the interference filter may be constructed with sectors adjacent to each other with each sector being transmissive for a respective trace gas. For simplicity, only one interference filter 31 is illustrated in FIG. 1. The concentration of individual trace gases 10' is determined in the electronic evaluation means 4 of a multi-component detector apparatus from linear combinations of the spectral intensity measured for the individual component/trace gas and, for example, are represented on an indicating unit 41. This indication may take place optically directly on a single display. The concentration of the residual gases may also be recorded continuously on a storage medium or the values of the concentrations can be fed directly to a computer 43 and further processed.

As shown in FIG. 1, the resistance 24 is connected to the electronic evaluation means 4 in parallel with the photosensor 32 in order to deliver a signal thereto representative of the current magnitude in the secondary circuit 22. In addition, an amplifier 44 is provided between the resistance 24 and the electronic evaluation means 4 for amplification of the resistance signal.

An alarm unit 42 may also be connected to the electronic evaluation means in order to trigger an alarm when concentration of one or more trace gases exceeds a pre-selected value.

Figure 2:
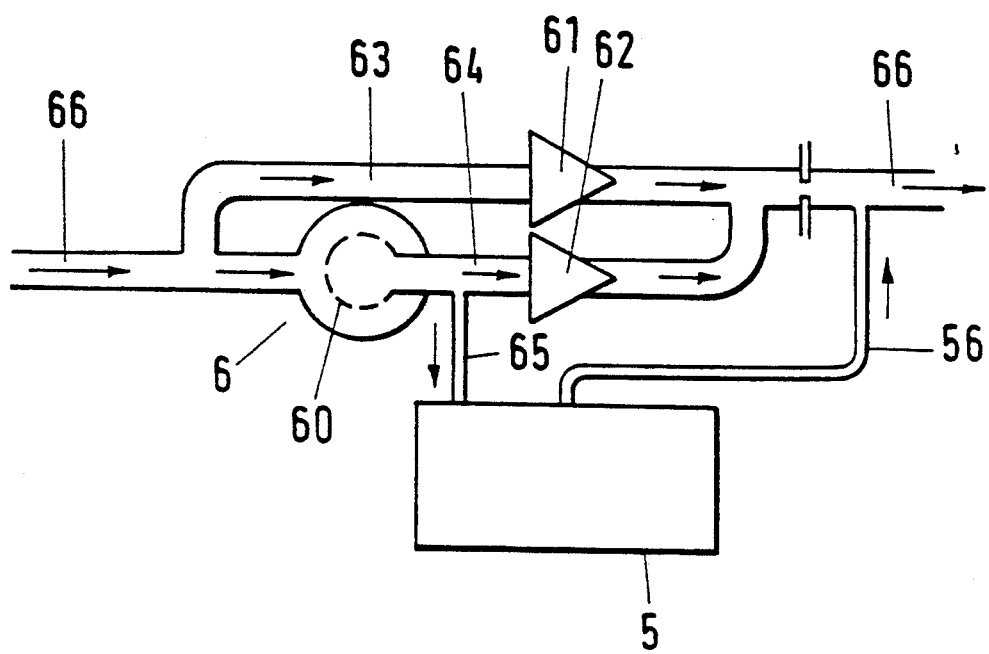

Referring to FIG. 2, the measuring device 5, for example, constructed as above may be utilized with an intermittently operating pyrolyzer 6 disposed upstream of the measuring chamber. Such a combination can be used for determining the concentration of traces of hydrocarbons in a gas as well as the proportion of aerosols. For example, fat-aerosols or oil-aerosols. In this case, the measure of the aerosol concentration takes place in two phases whereas the determination of the concentration of other residual gases proceeds on a continuous basis. Only the measurement of the aerosol proportion takes place intermittently.

The pyrolyzer 6 is essentially a metal filter 60 with a pore size in the region of 0.2 $\mu$ to 0.3 $\mu$, in which the aerosols are retained. The pyrolyzer 6 further comprises a sleeve-heating double-winding (not shown) which is mounted on the filter 60 by a bracing device. The temperature in the pyrolyzer 6 is measured internally at the metal filter 60 by a thermo-element (not shown).

The pyrolyzer 6 includes two branch lines 63, 64 which are connected in parallel within a main gas flow pipe 66 for the flow of the gas to be analyzed. In addition, valves 61, 62 are disposed within each branch line 63, 64 for shutting off the flow of gas therethrough on a selected basis. In addition, a branch line 65 is connected between one branch line 64 extending from the filter 60 and the measuring device 5 while a return line 56 extends from the measuring device 5 to the main pipeline 66.

In a first phase of operation, the pyrolyzer 6 is heated. During this time, aerosols are concentrated in the metal filter 60 with a mass flow, 100 times increased relative to the mass flow in the measuring branch 65. At this time, the valve 61 is closed and the valve 62 is opened so that no gas flows in the branch 63. A partial current of the aerosol-free gas flows through the return line 56 back to the main flow while the majority of the gas flows through the branch 64.

In the second phase, the pyrolysation of the aerosols takes place in volatile hydrocarbons at a temperature of, for example, 400° C. The valve 61 is opened in this phase and the valve 62 closed. The greatest part of the gas flows through the branch 63 and there is only a small measuring gas flow through the measuring branch 64 to the measuring device 5.

The temperature of the filter element 60 is correlated with the $C_xH_y$ signal in a computer, in the sense that the measuring period for the volatile hydrocarbon coming from the pyrolyzer, which has a finite time duration, only begins on reaching a predetermined threshold temperature. The $C_xH_y$ signal increases with the pyrolyzer if aerosols are enriched in the filter 60 of the pyrolyzer 6 in the first phase. The first phase may be in the region of 5 to 30 minutes and the second phase in the region of about 5 minutes.

The gas flows in the individual branches can be measured with gas flow meters of known kind (not shown). The pressure in the main gas flow pipe 66 may be in the region of 10 to 20 Bar and in the measuring branch 65, 56 may lie in the region of 1 to 2 Bar.

The evaluation method for a number of residual gas components 10′, as well as details of a device suitable therefor, are explained with reference to FIG. 3. This shows the variation of intensity of the emission spectrum of the light in the arc 15 in dependence on the wavelength. The wavelength in nano-meters (nm) is given on the abscissa. The symbols shown in brackets below the abscissa represent the interference filters used for determining various residual gases, with an indication of the wavelength in nm.

In the illustrated example the photoemission is measured at 431 nm, 427 nm, 405 nm, 376 nm, and 308 nm. On the basis of the obtained curves the concentration of the individual contaminants is determined with the aid of linear combinations of the measured intensities.

The bandwidth of the filter and the half value width (HWB) of the maxima at these frequencies are compared in the following table:

| Wavelengths | Half value width |
|---|---|
| 308 ± 2 nm | 5–10 nm |
| 376 ± 1 nm | 4–6 nm |
| 405 ± 1 nm | 4–6 nm |
| 427 ± 1 nm | 4–6 nm |
| 431 ± 1 nm | 4–6 nm |

The intensities measured at these frequencies are correspondingly designated by $I_{431}, I_{427}, I_{405}, I_{376}, I_{308}$. In these frequency regions, the representative photoemission of $N_2$, $N^+_2$, $I_{CH}$, $I_{OH}$ and $I_U$ and the continuous background U are measured, designated $I_N$, $I_{N+2}$, $I_{CH}$, $I_{OH}$ and $I_U$.

The following system of equations results from the measurements:

$$I_{431} = I_{HC} + a_1 I_N + I_U \quad (1)$$

$$I_{427} = I^+{}_{N2} + a_2 I_{CH} + I_U \quad (2)$$

$$I_{405} = a_5 I_{N2} + I_U \quad (3)$$

$$I_{376} = I_{N2} + I_U \quad (4)$$

$$I_{308} = I_{OH} + I_U \quad (5)$$

$a_1$, $a_2$, $a_3$ are constants. Possible further solution:

(a) Determining the gross pure intensities for CH and $N_2$ (Gross intensity = intensity of a trace gas with superimposed intensities of other gas/elements plus intensity of the background.

Gross pure intensity = intensity derived purely from a single specified trace gas plus intensity of the background):

$$(1) - a_1(2): I_{CH}(1 - a_1 a_2) + I_U(1 - a_1) = I_{431} - a_1 I_{427} \quad (6)$$

$$(2) - a_2(1): I_{N+2}(1 - a_1 a_2) + I_U(1 - a_2) = I_{427} - a_2 I_{431} \quad (7)$$

(b) Net intensities for $N_2$ and U (net intensity = intensity derived purely from a single specified trace gas, without intensity of the background).

$$(3) - a_5(4): I_U(1 - a_5) = I_{405} - a_5 I_{376} \quad (8)$$

$$(4) - (3): I_{N2}(1 - a_5) = I_{376} - I_{405} \text{ TM (9)}$$

The net intensities of the individual residual gases are obtained by subtraction of the equations for the intensity of the background (equation 8) from the equations for the intensities of the individual residual gas components (equations (6), (7), (9) and (5)).

The solution equations are linear combinations of the starting equations.

The concentrations of the contaminants are derived from the net intensities according to the general formula (given here only for Conc $N_2$ from $IN^+_2$ (Conc = concentration).

$$\text{Conc } N_2 = \frac{a_{N_2^+} + I_{N_2^+} - \left(1 + \sum_i b_i B_i\right)}{c_{N_2^+} + J - d_{N_2^+} I_{N_2^+} - \Sigma d_i I_i} \quad (10)$$

wherein:
$a_{N2}$ and $C_{N2}$ are empirical constants
J is the measured arc current
$b_i$, $d_i$ are the coefficients of the contaminant i
$I_i$ is the net intensity of the contaminant i
$H_2O$ and J are supplementarily taken into account.

Equation (10) can for example be realized in an analog circuit shown in basic form in FIG. 4. The amplifiers 71 to 78 as shown in the drawing are fed with the gross intensities ($I_{gross}$) and from them the gross pure intensities $I_{gross}$ pure) and net intensities ($I_{net}$) respectively are formed. This manner of signal handling can naturally also take place using digital technology.

Figure 5:
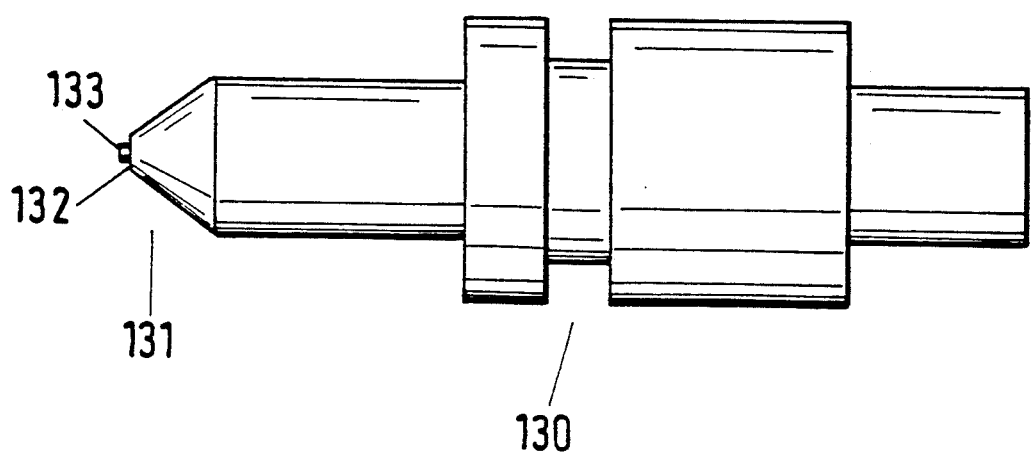
FIG. 5 illustrates an enlarged side view of an electrode for a device according to the invention.

Referring to FIG. 5, an electrode 130 which may be utilized in the measuring chamber of FIG. 1 may be constructed with a conically shaped end 131 of truncated cone shape having a flattened region 132. In addition, the conical end 131 may have an angle in the order of 70°. The electrode also has a cylindrical tip 133 having an end surface at least approximating the area of the base of the arc to be generated during operation.

The invention thus provides a device for the determination of impurities in gases such noble gases which is capable of a relatively long life. In this respect, the device is able to operate without need to change the electrodes on a frequent basis due to the generating of a low frequency low alternating voltage therein.

In addition, the invention provides an electronic evaluation means which includes an electrical circuit means for determining the concentration of gaseous impurities in accordance with a summation procedure of the measured intensities for the various impurities.

What is claimed is:

1. A device for determining impurities in a gas comprising
   a measuring chamber having a pair of electrodes defining a gap therebetween, an inlet for supplying gas into said chamber and an outlet for an outflow of gas from said chamber;
   a transformer for generating a low frequency alternating voltage, said transformer having a secondary circuit connected to said electrodes for generating an arc between said electrodes to effect an emission spectrum of the gas in said gap and wherein at least one electrode has a conically shaped end with a cylindrical tip having an area approximately equal to the base of said generated arc; and
   means for measuring and evaluating the emission of spectrum of the gas to determine the concentration of impurities therein.

2. A device for determining impurities in a gas comprising
   a measuring chamber having an electrode therein for generating an electrical discharge in a gas to be measured, said electrode having a conically shaped end of flattened truncated cone shape with a cylindrical tip having a surface at least approximating the area of a base of an arc generated during operation;
   a low frequency alternating voltage source connected to said means; and
   means for measuring and evaluating an emission spectrum of the gas in said electrical discharge.

3. A device as set forth in claim 1 wherein said electrode end has an angle of about 70°.

4. A device for determining impurities in a gas comprising
   a measuring chamber having means therein for generating an electrical discharge in a gas to be measured, said measuring chamber including an inlet for a continuous supply of gas into said chamber and an outlet for a continuous outflow of gas from said chamber, wherein said means in said chamber includes an electrode having a conically shaped end with a tip having a surface at least approximating the area of a base of an arc generated during operation, and wherein said electrode end is of flattened truncated cone shape and said tip is cylindrical and is on said end;
   a source of alternating voltage connected to said means, said voltage alternating at a frequency which is less than 1,000 Hertz;
   a spectral filter for filtering the emission spectrum generated in said measuring chamber;
   a photodiode downstream of said filter for generating an electrical signal in response to the filter emission spectrum; and
   means for measuring and evaluating an emission spectrum of the gas in said electrical discharge.

5. A device as set forth in claim 4 wherein said electrode end has an angle of about 70°.

6. A device as set forth in claim 4 wherein the means for evaluating includes means for determining the concentration of at least one impurity in the gas.

* * * * *

UNITED STATES PATENT AND TRADEMARK OFFICE
CERTIFICATE OF CORRECTION

PATENT NO. : 5,168,323

DATED : December 1, 1992

INVENTOR(S) : Purtschert et al.

It is certified that error appears in the above-indentified patent and that said Letters Patent is hereby corrected as shown below:

Column 1, line 23, change "Helium" to --Helium,--;
          line 23, change "described ," to --described,--;
          line 26, change "gas and" to --gas, and--;
          line 37, change "is" to --are--;

Column 2, line 58, change "With" to --with--;

Column 3, line 9, change "wave" to --wave- --;
          line 23, change "e.g." to --e.g.,--;

Column 4, line 3, after "frequency" insert --alternating voltage. At the same time, a gas is passed through--;

line 48, after "when" insert --the--;

Column 6, line 24, change "intensity =intensity" to --intensity=intensity--;
          line 39, delete "TM"; same line move "(9)" to right hand margin;
          line 51, change "centration)." to --centration)).--;

Column 7, line 1, change "$I_{gross}$ pure)" to --($I_{gross\,pure}$)--;
          line 13, change "gases such noble gases" to --gases, such as noble gases,--

UNITED STATES PATENT AND TRADEMARK OFFICE
CERTIFICATE OF CORRECTION

PATENT NO. : 5,168,323
DATED : December 1, 1992
INVENTOR(S) : Purtschert et al.

It is certified that error appears in the above-indentified patent and that said Letters Patent is hereby corrected as shown below:

Column 7, line 17, after "frequency" insert --,--.

Signed and Sealed this

Fifth Day of July, 1994

Attest:

BRUCE LEHMAN

Attesting Officer  Commissioner of Patents and Trademarks